(12) United States Patent
Aneja

(10) Patent No.: US 6,384,260 B1
(45) Date of Patent: May 7, 2002

(54) MOLECULAR PROBES AND MODULATORS FOR PI-PLC AND PI 3-KINASE

(75) Inventor: Rajindra Aneja, Ithaca, NY (US)

(73) Assignee: Nutrimed Biotech, Ithaca, NY (US)

( * ) Notice: Subject to any disclaimer, the term of this patent is extended or adjusted under 35 U.S.C. 154(b) by 0 days.

(21) Appl. No.: 09/826,396

(22) Filed: Apr. 3, 2001

Related U.S. Application Data

(63) Continuation of application No. 08/872,222, filed on Jun. 10, 1997, now Pat. No. 6,232,486.
(60) Provisional application No. 60/019,651, filed on Jun. 11, 1996.

(51) Int. Cl.$^7$ ................................................. C07F 9/117
(52) U.S. Cl. ....................... 558/160; 558/161; 558/179; 558/180; 558/186
(58) Field of Search ................................. 558/160, 161, 558/179, 180, 186

(56) References Cited

U.S. PATENT DOCUMENTS

| | | | |
|---|---|---|---|
| 4,515,722 A | 5/1985 | Yang et al. | |
| 5,053,399 A | 10/1991 | Kozikowski | |
| 5,227,508 A | 7/1993 | Kozikowski et al. | |
| 6,245,754 B1 * | 6/2001 | Kozikowski et al. | 514/120 |
| 6,288,046 B1 * | 9/2001 | Jackson et al. | 514/120 |

OTHER PUBLICATIONS

Bruzik & Tsai, "Toward the Mechanism of Phosphoinositide–Specific Phospholipases C," *Bioorganic & Medicinal Chemistry*, vol. 2, No. 2, pp. 49–72, 1994.

Chen et al., Synthesis of Photoactivatable 1,2–0–Diacyl-sn–glycerol Derivatives of 1–L–Phosphatidyl–D–myo-inositol 4,5–Bisphosphate (PtdInsP$_2$) and 3,45–Trisphosphate (PtdInsP$_3$), *J. Org. Chem.*, vol. 61, pp. 6305–6312, 1996.

Gadella et al., "Enzymatic Synthesis of Pyrene–Labeled Polyphosphoinositides and Their Behavior in Organic Solvents and Phosphatidylcholine Bilayers," *Biochemistry*, vol. 29, pp. 3389–3395, 1990.

Gu & Prestwich, Synthesis of Phosphotriester Analogues of the Phosphoinositides PtdIns (4,5) P$_2$ and PtdIns (3,4,5) P$_3$, *J. Org. Chem.*, vol. 61, pp. 8642–8647, 1996.

Hendrickson et al., "Kinetics of *Bacillus cereus* Phosphatidylinositol–Specific Phospholipase C with Thiophosphate and Fluorescent Analogs of Phosphatidylinositol," *Biochemistry*, vol. 31, pp. 12169–12172, 1992.

Shashidhar et al., "A chromogenic substrate for phosphatidylinositol–specific phospholipase C: 4–nitrophenyl myo–inositol–1–phosphate,"*Chem. Phys. Lipids*, vol. 60, pp. 101–110, 1991.

* cited by examiner

Primary Examiner—Deborah C. Lambkin
(74) Attorney, Agent, or Firm—Williams, Morgan and Amerson

(57) ABSTRACT

This invention provides analogues of phosphatidylinositol-phosphates modified at one or more selected inositol-hydroxyls and optionally carrying reporter or anchoring groups attached in the lipid or the inositol residues, and, the synthetic intermediates and methods for the preparation of these analogues. The analogues are useful as research reagents in biomedical studies related to structure, function and therapeuticals, including reference materials for analyzing the metabolic products in safety and efficacy studies of 2- and/or 3-hydroxyl modified inositols and phosphatidylinositols as drug candidates.

43 Claims, 2 Drawing Sheets

Figure 1:
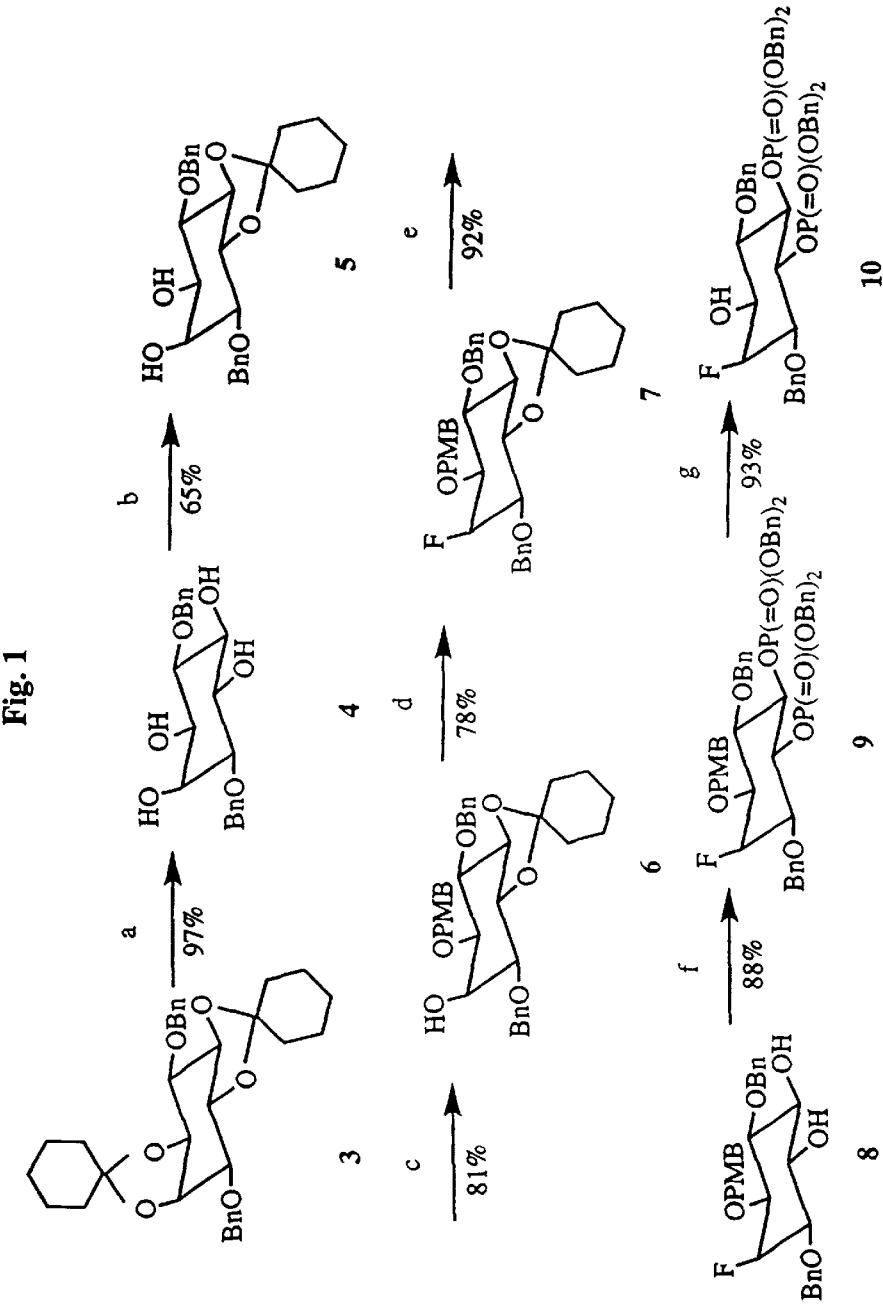

Scheme I: Synthesis of 1D-3,6-di-*O*-benzyl-2-deoxyfluoro-*myo/scyllo*-inositol-4,5-bis(dibenzylphosphate) 10. *Reagents and Conditions*: (a) HOAc/H$_2$O (90:10), 95 °C. (b) Cyclohexanone dimethylketal (1.2 eq.), DMSO, 40-45 °C, red. press. (c) Bu$_2$SnO, toluene, 110 °C, DMF, 4-MBnCl, CsF, 80 °C. (d) CH$_2$Cl$_2$, DAST, NEt$_3$, 35-40 °C. (e) Ethylene glycol (1.1 eq.), *p*-TSA, CH$_2$Cl$_2$, R.T. (f) (*i*-Pr)$_2$NP(OBn)$_2$, 1*H*-tetrazole, CH$_2$Cl$_2$, -40 °C, *m*-CPBA. (g) DDQ, CH$_2$Cl$_2$, R.T.

Scheme II: Synthesis of 1,2-di-O-hexanoyl-sn-glycero-3-phosphoric acid (15) and 1-O-hexanoyl-2-O-(ω-Cbz-aminobutanoyl)-sn-glycero-3-phosphoric acid (18). *Reagents and Conditions*: (a) NaOAc buffer pH 8.5, 37 °C, PLD. (b) Ether-NaOAc buffer pH 8.5, 37 °C, PLA$_2$. (c) ω-Cbz-aminobutanoic acid, DCC, DMAP, CHCl$_3$, R.T.

MOLECULAR PROBES AND MODULATORS FOR PI-PLC AND PI 3-KINASE

The present application claims priority to application Ser. No. 08/872,222, filed Jun. 10, 1997 now U.S. Pat. No. 6,232,486; which claims priority to provisional application Serial No. 60/019,651, filed Jun. 11, 1996.

This invention was partially made with finds provided by the Department of Health and Human Services under Grant No. NIH-GM51138. Accordingly, the United States Government has certain rights in this invention.

BACKGROUND OF THE INVENTION

This invention is concerned with certain structural and stereochemical analogues of the phosphoinositide group of cellular lipids, novel approaches for their preparation by synthesis and key starting materials and intermediates of these approaches. The phosphoinositides comprising 1D-1-(1', 2'-di-O-fattyacyl-sn-glycero-3'-phospho)-myo-inositols or phosphatidylinositol (PtdIns) and its mono- and poly-phosphate derivatives are key participants in the intracellular signaling cascade which is generated in response to stimulation of certain cell surface receptors by many agonists. Biosynthetic and metabolic transformations of the phosphoinositides are implicated in initiating, sustaining and regulating this signal cascade in an agonist and tissue specific manner. These lipid transformations are catalyzed by several families of enzymes including the phosphatidylinositol-specific phospholipase C (PI-PLC) and the phosphatidylinositol 3-kinase (PI 3-kinase). Stimulated hydrolysis of phosphatidylinositol-4,5-bisphosphate (PtdIns(4,5)P), the substrate preferred by the mammalian PI-PLC, is representative. This hydrolysis rapidly and simultaneously generates inositol-1,4,5-trisphosphate ($P_3$) and sn-1,2-diacylglycerol (DAG). Both $IP_3$ and DAG are second messengers respectively inducing Ca: mobilization from intracellular stores and protein kinase C (PKC) activation and are implicated in many physiological responses including mitogenesis (Berridge, 1984; Nishizuka, 1983). Specific PI-PLC enzymes function also in releasing membrane-anchored proteins using glycosyl-PtdIns as the anchoring ligand. PI 3-kinase specifically associates with and is phosphorylated by activated growth factor receptors and on coproteins which manifest protein-tyrosine kinase activity (Whitman et al, 1988; Auger et al, 1989). It phosphorylates $PtdIns(4,5)P_2$ specifically at the D-3 hydroxyl to produce phosphatidylinositol-3,4,5-trisphosphate ($PtdIns(3,4,5)P_3$) which is the putative novel and critical second messenger of growth signals (Auger et al, 1989; Carpenter and Cantley, 1990; Coughlin et al, 1989; Majerms, 1992). A complex role for PI 3-kinase and its products, the 3-phosphorylated phosphoinositides (3PPI), is emerging in the control of cell division and growth (Carpenter and Cantley, 1996). Additionally a role is seen for PI 3-kinase in transient actin polymerization and association between actin and cellular cytoskeletal elements, and a possible connection between this and the role in cell growth. Thus there is tremendous current interest in elucidating the structure, biochemical behavior, and physiological roles of the various isoforms of these key enzymes and in tracing the downstream targets of the products of their action on the phosphoinsoitides. Probes and modulators incorporating the core $PtdIns(4,5)_2$ structure as provided by the present invention are required for these multifarious ongoing research investigations.

Endogenous $IP_3$ is dephosphorylated and is reutilized with DAG for the resynthesis of PtdIns, the PtdIns is rephosphorylated to PtdIns-phosphates, and the latter are converted back to PtdIns by the action of PtdIns-phosphate phosphatases, in the overall PtdIns metabolic cycle. Exogenous inositols and PtdIns, including structurally modified analogues such as those disclosed in Kozikowski (U.S. Pat. No. 5,053,399), Kozikowski et al (U.S. Pat. No. 5,227,508), and, Yang et al (U.S. Pat. No. 4,515,722) are incorporated into the PtdIns cycle and ostensibly into the PtdIns-phosphate pool. The characterization of the biosynthetic PtdIns-phosphates produced from the aforementioned modified exogenous inositols and PtdIns derivatives requires the corresponding modified-$PtdIns(4,5)P_2$ and related derivatives as reference reagents. These reference reagents are provided by the present invention.

In the prior art (Yang et al, U.S. Pat. No. 4,515,722) synthesized 2-modified analogues of PtdIns and found these to be useful antiinflammatory/analgesic agents. These analogues all incorporated DL-inositol moieties and the preferred lipid moiety was 1-(3',4'-acyloxybutylphosphonyl. The same biological activity was also claimed for unspecified PtdIns-phosphate derivatives but no application as a research reagent was disclosed.

Several phosphoinositide analogues are known in the prior art relevant to the present invention. The fluorescent 1-pyrenebutyl myo-inositol-1-phosphate and the chromogenic 4-nitrophenyl myo-inositol-1-phosphate have been described as reagents for the assay of bacterial PI-PLC (Hendrickson et al, 1992; Shashidhar et al, 1991) but are poor substrates and considered to be inadequate reagents (Bruzik and Tsai, 1994). The preparation of a nanomolar quantity of a pyrene-labelled $PtdIns(4,5)P_2$ from the corresponding pyrene-labelled PtdIns by successive phosphorylations at 4-O and 5-O by partially purified PtdIns 4-kinase and PI 5-kinase has been reported also (Gadella et al, 1990) but the required enzyme reagents and method of preparation are not easily accessible. Synthetic $PtdIns(4,5)P_2$ labelled with photoactive p-benzoyldihydrocinnamoyl and related reporter groups covalently attached to either the 1'-acyloxy or the 1-phosphate have been reported recently (Gu and Prestwich, 1996; Chen et al, 1996). These analogues are broadly similar, but attachment of the reporter group at 1-phosphate creates a 1-phosphotriester analogue and thereby destroys the core 1-phosphodiester function which is an essential structural feature of $PtdIns(4,5)P_2$ and all phosphoinositide substrate of PI-PLC.

It is considered that a sufficient range of appropriate biochemical probes and modulators of these enzymes are not available (Bruzik and Tsai, 1994). Therefore, an objective of the present invention is to provide substrate analogues as structure/mechanism-based probes and modulators suitable for research studies on PI-PLC, PI 3-kinase and related enzyme families. Additional objectives are to provide novel approaches for their preparation by synthesis and key starting materials and intermediates of these approaches.

SUMMARY OF THE INVENTION

This invention comprises several synthetic analogues of the preferred phosphoinositide substrates of the mammalian PI-PLC and PI 3-kinase enzyme families, exemplified by $PtdIns(4,5)P_2$, which retain the core structural requirements for efficient bonding and catalysis, but in which the 2-OH is rendered non-nucleophilic by derivatization or replacement exemplified by 2-OAc and 2-deoxyfluoro respectively, and, which may additionally contain photoaffinity, fluorescent, spin, other reporter groups, and conjugands for linking to polymer, chromatographic matrix, or gold surfaces are incorporated in the fatty acyl or inositol residues as shown in structure. Thus, the invention provides substrate analogues as structure/mechanism-based probes and modulators suitable for research studies on PI-PLC, PI 3-kinase and related enzyme families. Additionally, it provides novel approaches for their preparation by synthesis, and key starting materials and intermediates of these approaches.

A BRIEF DESCRIPTION OF THE DRAWINGS

FIG. 1. Scheme I: Synthesis of 1D-3,6-di-O-benzyl-2-deoxyfluoro-myo-inositol-4,5-bis(dibenzylphosphate) 10.

Figure 2:
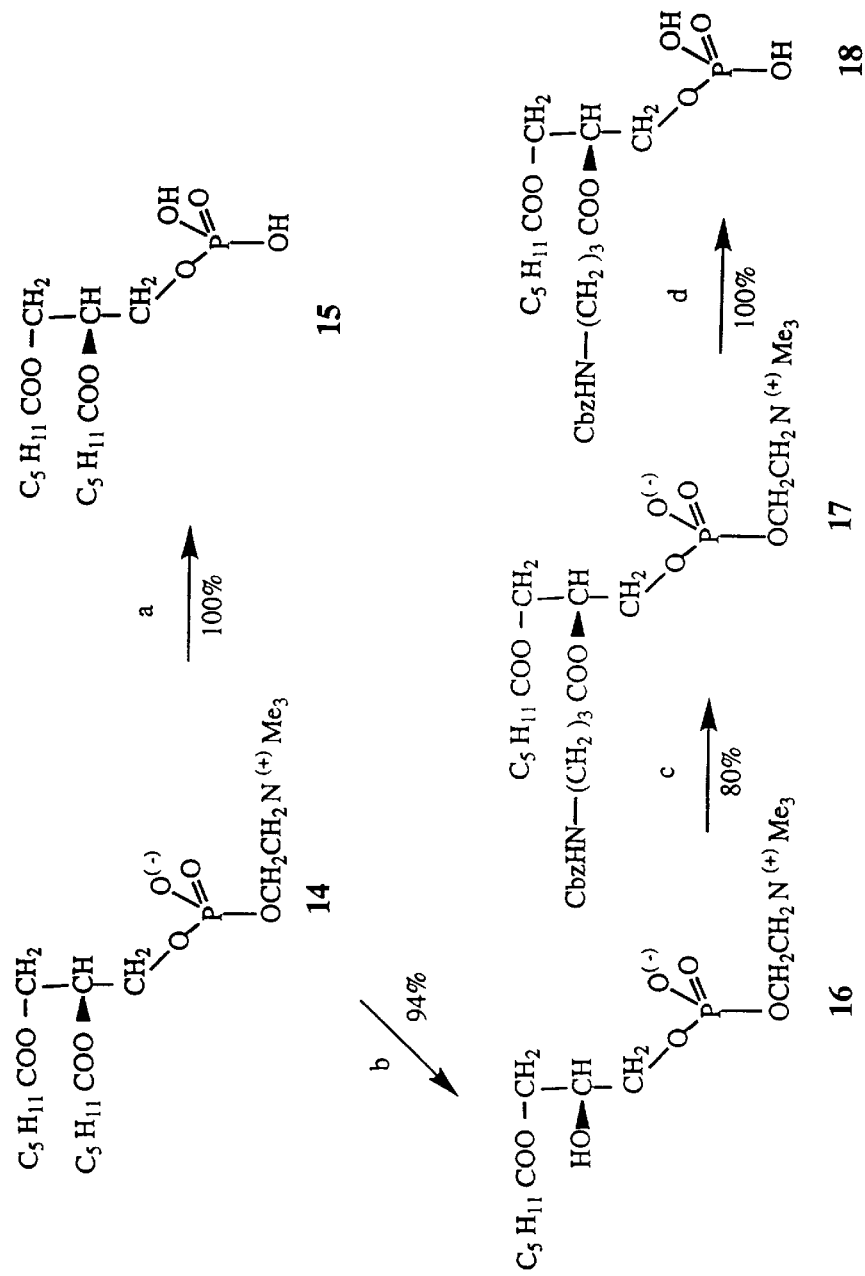

FIG. 2. Scheme II: Synthesis of 1,2-di-O-hexanoyl-sn-glycero-3-phosphoric acid (15) and 1-O-hexanoyl-2-O-(ω(-Cbz-aminobutanoyl)-sn-glycero-3-phosphoric acid (18).

DETAILED DESCRIPTION OF THE INVENTION

Phosphatidyl-myo-inositol-4,5-bisphosphate (PtdIns(4,5)$P_2$) is a vital participant in intracellular signalling and allied processes, functioning as the preferred substrate of the mammalian phosphoinositide-specific phospholipase C (PI-PLC) and phosphoinositide 3-kinase (PI 3-kinase) enzymes, and, as allosteric activating factor of cellular regulatory proteins with and without pleckstrin homology domains.

In one embodiment, this invention comprises several synthetic analogues of PtdIns(4,5)$P_2$ (1, X=OH, $R^1$, $R^2$=Alkyl-C=O) incorporating one or more of the following modifying structural features: (i) the 2-OH is rendered non-nucleophilic by derivatization or replacement exemplified by 2-OAc and 2-deoxyfluoro respectively, and (ii) photoaffinity, fluorescent, spin, other reporter groups, and conjugands for linking to polymer, chromatographic matrix, or gold surfaces are incorporated in the fatty acyl or inositol residues as shown in structure 2.

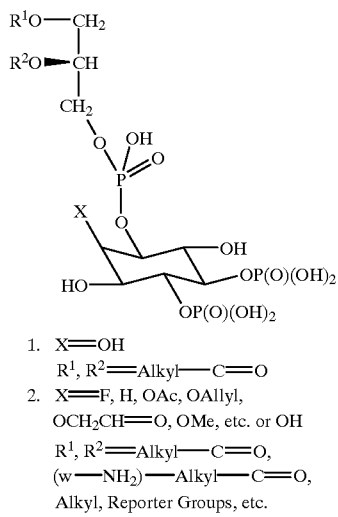

1. X═OH
   $R^1$, $R^2$═Alkyl—C═O
2. X═F, H, OAc, OAllyl,
   OCH$_2$CH═O, OMe, etc. or OH
   $R^1$, $R^2$═Alkyl—C═O,
   (w—NH$_2$)—Alkyl—C═O,
   Alkyl, Reporter Groups, etc.

These analogues have utility as research reagents as structure- and mechanism-based competitive inhibitors of the mammalian PI-PLC, applicable inter alia as comparative probes of enzyme-action and protein-binding in PI-PLC, as novel substrate analogues of PI 3-kinase, and general probes of PtdIns(4,5)$P_2$-binding to cellular regulatory proteins. In the prior art, deoxyfluoro-inositols (Kozikowski et al, U.S. Pat. No. 5,053,399), and deoxyfluoro-phosphatidylinositols (Yang et al, U.S. Pat. No. 4,515,722; Kozikowski et al, U.S. Pat. No. 5,227,508) have been described. These are being developed as therapeutic agents and their metabolic products must be identified. The analogues disclosed in the present invention are likely metabolic products of the aforementioned prior art therapeuticals and therefore have utility as critical reference materials in analyses for establishing the presence or absence of such metabolic products. Several studies have provided information on the structural features of the substrate which are essential for PI-PLC enzyme activity. Most of the early findings were obtained with PI-PLC from bacterial sources although identical conclusions are emerging for the guinea pig uterus PI-PLC and the cloned isoforms. The consensus view has developed that the inositol-1-phosphate residue is required for substrate recognition as well as catalytic action. The presence of the free 2-OH is essential for catalytic action. Nucleophilic attack by this OH on the 1-phosphate phosphorus leads to the inositol-1:2cyclic-phosphates which are the diagnostic products of bacterial PI-PLC action (Lin et al, 1990; Volwerk et al, 1990). Binding to a lipid bilayer or equivalent lipid aggregate containing the substrate is essential for high activity. The crystal structure of the PI-PLC from *Bacillus cereus* in complex with its hydrolysis product, that is myo-inositol, has been solved to 2.6 Å (Heinz et al, 1995). This suggests that His32 acts as general base, accepting a proton from the myo-inositol 2-OH of PtdIns. Nucleophilic attack by the deprotonated 2-O on the phosphatidyl phosphorus results in a 5-cyclic phosphate and cleavage of DAG. Crystal structure of a mammalian PI-PLCd1 deletion mutant in complex with its hydrolysis product, that is IP$_3$, has been determined (Essen et al, 1996; Grobler et al, 1996), and the complexes with Ins(1:2cyc)P and its 2-methylene analogue of have been studied (Essen et al, 1997). The data suggest a need and a mechanism for membrane attachment and for Ca$^{2+}$-dependent hydrolysis of PtdIns(4,5)$P_2$. In the proposed reaction mechanism, the 2-OH group is deprotonated in the first step by an internal general base, followed by nucleophilic attack on the 1-phospho group and release of DAG.

Another embodiment of this invention comprises two complementary strategies for syntheses illustrated for 2-deoxyfluoro and 2-OAc type analogues respectively. The approach for synthesis of the 2-deoxyfluoro PtdIns(4,5)$P_2$ (2, X=F) and analogues involves the preparation of (i) optically resolved O-protected myo-inositol-4,5-bisphosphate with a free 1-OH and (ii) 1,2-di-O-fattyacyl-sn-glycero-3-phosphoric acid (sn-3-phosphatidic acid), as inositol and lipid synthons respectively, (iii) coupling of the inositol 1-OH and the lipid phosphoric acid by phosphodiester condensation, and (iv) deprotection of the condensation product to obtain the target PtdIns(4,5)$P_2$ analogue. This approach is suitable for other analogues also including the 2-OAlkyl types. The 2-OCOR types illustrated by 2-OAc (2, X=OAc) are best prepared from a synthetic PtdIns(4,5)$P_2$ derivative in which the 3, 4, 5, and 6-OH or derived phosphates selectively carry temporary protecting groups and the unprotected 2-OH is rendered non-nucleophilic by derivatization to an ester or equivalent, followed by removal of the temporary protecting groups.

In yet another embodiment of this invention, the synthetic 2-modified analogues of PtdIns(4,5)$P_2$ and corresponding analogues lacking the 2-modification (2, X=OH) are offered as matched pairs.

Yet another embodiment of the invention comprises derivatives of PtdIns(4)P, and PtdIns(3)P series analogous to the PtdIns(4,5) series above.

The key inositol synthon for the 2-deoxyfluoro series was prepared from 1D-3,6-di-O-benzyl-1,2:4,5-dicyclohexylidene-myo-inositol 3 (Aneja et al, 1995) as outlined in Scheme I, FIG. 1. The two 2-deoxyfluoro epimers produced by the DAST reaction were separated by HPLC and the 2-epimer being the 2-deoxyfluoro-scyllo-inositol analogue was the major product.

The synthesis of 1,2-di-O-hexanoyl-sn-glycero-3-phosphoric acid (15) and 1-O-hexanoyl-2-O-(ω-Cbz-aminobutanoyl)-sn-glycero-3-phosphoric acid (18), outlined in Scheme II, FIG. 2, illustrates the general approach to sn-3-phosphatidic acids is adapted from literature methods (Aneja, 1974).

The inositol and lipid synthons were coupled using triisopropylbenzene-sulfonyl chloride in anhydrous pyridine at R.T (Aneja et al, 1997). The product was subjected to Pd-C catalyzed hydrogenolysis to remove the benzyl ether-ester protecting groups to obtain 2 (example, X=F, $R^1=R^2=C_{15}H_{31}CO$).

The structure of the inositol synthon 10 may be varied by replacing reaction of 6 with DAST in Scheme I step d by other reagents to produce 2-deoxy, oxo, O-acyl, O-alkyl, deoxyhalo or deoxydihalo analogues of the inositol synthon 10. Benzylation of 6 yielded the 2-O-benzyl analogue 11 of 7. Subsequent transformations exactly as in Scheme I gave 1D-2,3,6-tri-O-benzyl-myo-inositol-4,5-bis(dibenzylphosphate) 12, the key inositol synthon for PtdIns(4,5)$P_2$ unmodified in the inositol residue.

With 18 as the sn-3-phosphatidic acid, the products of condensation-hydrogenolysis yielded 1-O-hexanoyl-2-O-(aminobutanoyl)-sn-3-phosphatidyl-based PtdIns(4,5)$P_2$s; reaction of the primary amino group in these with "activated" reporter ligands gave the labelled analogues; for example reaction with N-hydroxysuccinimidyl-4-azidosalicylic acid gave the 4-azidosalicyl photoaffinity-labelled analogue.

In the second strategy for synthesis, 1D-(1,2-dihexadecanoyl-sn-glycero-3-phospho)-myo-inositol-3,6-di-O-benzyl-4,5-bis(dibenzylphosphate) was prepared by the method reported for the dihexanoyl derivative (Toker et al. 1994). On treatment with an OH acylating reagent, for instance $AC_2O$-DCC-DMAP, it gave the 2-O-acetyl derivative, which was hydrogenolyzed to the 2-OAc analogue of PtdIns(4,5)$P_2$ (2, X=OAc, $R^1=R^2=C_{15}H_{31}CO$). The short-chain acyloxy derivatives are prone to non-specific chemical hydrolysis.

The strategies for synthesis may be adapted for analogues incorporating reporter groups linked to the inositol residue in PtdIns(4,5)$P_2$s, for instance, by employing the 6-O-di-N-bezylaminoalkyl analogue of 3 as the starting material.

The utility of the key intermediates is refelcted in the synthesis of the target PtdIns-phosphate analogues. The condensation products of the sn-3-phosphatidic acids and the optically resolved O-protected myo-inositol4,5-bisphosphate with an additional free hydroxyl are particularly useful for incorporating other types of labels, such as radioactive or stable isotope based groups.

The action of PI-PLC on PtdIns(4,5)$P_2$ produces $IP_3$ and DAG. Ostensibly this involves intramolecular nucleophilic attack on the 1-phosphodiester by the 2-OH (Essen et al, 1996). The 2-modified analogues of PtdIns(4,5)$P_2$ of the present invention preclude the intramolecular nucleophilic action. As the core PtdIns(4,5)$P_2$ structure is retained, efficient interaction with the catalytic and allosteric binding sites results. Additional design and performance features may be incorporated for special applications, as in 1D-1-(1,2-di-O-n-butyl-sn-glycero-3-phospho)-2-deoxyfluoro-scyllo-inositol-4,5-bisphosphate prepared as a water-soluble analogue, stable to non-specific chemical hydrolysis, and useful for the preparation of co-crystallizates with PI-PLC isozymes for X-ray crystal structure analysis.

For use as analytical research reagents, the behavior of the 2-modified PtdIns(4,5)$P_2$ analogues in analytical chromatography was established. Thin layer chromatography is carried out preferably on silicagel layers with organic binder and impregnated with potassium oxalate and EDTA as scavengers for adventitious silica. These thin layer plates can be prepared from commercial TLC plates, preferably Cat. No. 47031, Uniplate from Analtech Inc., Newark, N.J. by dipping briefly in a solution of $K^+$oxalate (1%) and $Na_4$ EDTA (0.6%) in methanol-water (3:2) followed by air-drying for 24 Hr. The plates are spotted with the analogue (1 to 10 mg) in solvent ($CHCl_3$—$CH_3OH$—$H_2O$, 2:1:0.2), development with eluant $CHCl_3$—$CH_3OH$-28% $NH_4OH$—$H_2O$ (2:2:1:1) at room temperature, and, visualization with $I_2$ vapor or other appropriate reagent. The Rf of unmodified PtdIns(4,5)$P_2$ is ca. 0.5, for analogues with w-aminoalkyl residues the Rf is in the range 0.2 to 0.3, and the presence of 2-deoxyfluoro substituent raises the Rf by ca. 0.05 to 0.1 compared with the 2-OH series. The TLC conditions can be translated into protocols for liquid chromatography including high performance liquid chromatography (HPLC) by techniques which are well known to practitioners of chromatographic separation.

For co-crystallization with PI-PLC isozymes, the water soluble 2-deoxyfluoro dibutylether PtdIns(4,5)$P_2$ analogue may be added as a solution in buffer to the enzyme solution. Other protocols may be applied to suit individual experiments.

The invention has been delineated with reference to certain specific and preferred embodiments and methods. However, it is stated that many modifications and variations may be made while remaining within the scope and spirit of the invention.

All referenced patents and publications are incorporated herein by citation.

EXAMPLES

1D-3,6-Di-O-benzyl-myo-inositol 1D-3,6-di-O-benzyl-1,2:4,5-di-O-cyclohexylidene-myo-inositol (5.0 g, 0.0096 mol), prepared by a literature procedure (Aneja et al, Tetrahedron Asymmetry (1995) 6, 17–18) was dissolved in 60 ml $HOAc$-$H_2O$ (9:1) and heated at 95–100° C. for 1 hr. The solution was evaporated to dryness under reduced pressure and the residue co-evaporated with $H_2O$, $CHCl_3$ and $CH_3OH$ to dryness. The crude residue of virtually pure 1D-3,6-di-O-benzyl-myo-inositol was used without purification: $[\alpha]_{589}$ +11.76° (c 1.9, $CHCl_3$—$CH_3OH$ 1:1). MALDI TDF MS m/z 361, $^1H$ NMR (300 MHz, $CDOD_3$) δppm 3.205 (d, 1H), 3.235 (d, 1H), 3.41 (d, 1H), 3.445 (d, 1H), 3.586–3.661 (q or dd) 3.71–3.90 (ψt, J 9.7 and 9.7 Hz), 4.02–4.18 (ψt, J 2.69 and 2.14 Hz), 4.62–4.75 (q, 4H), 7.14–7.62 (m 10 H).

1D-3,6-Di-O-benzyl-4,5-O-cyclohexylidene-myo-inositol

To a solution of 1D-3,6-di-O-benzyl-myo-inositol (4.1 g, 0.011 mol) and cyclohexanone dimethylketal 8 ml (0.05 mol) in dry DMSO (20 ml), p-toluene sulphonic acid monohydrate (pTSA) (35 mg) was added. The mixture was evacuated at 40–42° C. (red. pressure) for 5 hr. The solution was neutralized with saturated $NaHCO_3$ solution and left at 0–5° C. overnight. The products were extracted with ethyl acetate, organic layer was dried over $Na_2SO_4$ and solvent evaporated. Resulting glassy material was triturated with $CH_2Cl_2$ which dissolved the cyclohexylidene derivatives and the mixture was filtered to remove the insoluble starting material (1.1 g). TLC (CH$_2$Cl$_2$-ethyl acetate 1:1) of the solution showed 1D-3,6-di-O-benzyl-1,2:4,5-O-cyclohexylidene-myo-inositol (R$_f$=0.9), a major product (R$_f$=0.75), another product(R$_f$=0.55) and trace of the starting material(R$_f$=0.2). The CH$_2$Cl$_2$ soluble material chromatographed on Silicagel 60 Å in ethyl acetate-CH$_2$Cl$_2$ (1:4) gave the dicyclohexylidene derivative (0.150 g) and then the 1D-3,6-di-O-benzyl-4,5-O-cyclohexylidene-myo-inositol (2.27 g, 65%). Further elution with the same solvent in ratio 1:2 gave 1D-3,6-di-O-benzyl-1,2-O-cyclohexylidene-myo-inositol (Aneja et al, loc. cit.) (0.450 g, 13%). [α]$_{589}$ −33.2° (c 1.3,CHCl$_3$); MALDI TDF MS m/z 462.54, calc. 463.22 (M+Na)$^+$, $^1$H NMR (300 MHz, CDCl$_3$) δppm 1.44–1.85 (br,10H), 2.66(m,2H), 3.38(t, J 9.66 and 9.67, 1H), 3.54–3.61(m, 2H), 3.81(t, J 8.6 and 9.7, 1H), 4.05(t, J 9.67 and 9.67, 1H), 4.21(ψt, 1H), 4.72(d, 2H), 4.95(q, 2H), 7.26–7.44 (m, 10H).

1D-3,6-Di-O-benzyl-4,5-O-cyclohexylidene-1-p-methoxybenzyl)-myo-inositol

A mixture of 1D-3,6-di-O-benzyl-4,5-O-cyclohexylidene-myo-inositol (2.35 g,0.0053 mol), Bu$_2$SnO (1.33 g, 0.0053 mol) and toluene (70 ml) was stirred under reflux with a Dean-Stark apparatus for azeotropic removal of the water for 2 hrs and then evaporated to dryness under reduced pressure. To the residue was added DMF (40 ml), CsF (2.43 g, 0.016 mol) and 4-methoxybenzyl chloride (1.2 ml, 0.0088 mol) at 0–5° C. The reaction mixture was warmed and stirred at 40° C. for 2 hrs and 1 hr at 60° C. The solution was cooled to r.t. and diluted with 100 ml CH$_2$Cl$_2$, washed with water, dried over Na$_2$SO$_4$ and concentrated. The crude product was chromatographed on Silicagel 60 Å using gradient elution with CH$_2$Cl$_2$-acetone (99:1 to 95:5) producing 1D-3,6-di-O-benzyl-4,5-O-cyclohexylidene-1-(p-methoxybenzyl)-myo-inositol, 2.37 g (79%): [α]$_{589}$ −12.03° (c 1.11, CHCl$_3$) HMRS FAB$^+$ m/z 583.52, calc. (M+Na)$^+$ 583.277, $^1$H NMR (300 MHz, CDCl$_3$) δppm 1.40–1.83 (br,10H), 2.64 (br,1H), 3.28–3.46 (m,2H), 3.48–363 (dd or q 1H), 3.75–3.89 (s,3H), 3.96 (ψt, J 8.59 and 9.67, 1H), 4.05–4.27 (m 2H), 4.55–5.08 (m, 6H), 6.74–7.00 (m, 2H), 7.13–7.58 (m, 12H).

1D-3,6-Di-O-benzyl-2-deoxy-fluoro-4,5-O-cycloxylidene-1-O-(p-methoxybenzyl)-myo/scyllo-inositol To 1D-3,6-di-O-benzyl-4,5-O-cyclohexylidene-1-(p-methoxybenzyl)-myo-inositol (0.9857 g, 0.00176 mol) in 25 ml toluene under nitrogen atmosphere and at r.t. was added diethylaminosulphur trifluoride (0.35 ml, 0.0026 mol). The reaction mixture was stirred at r.t. for 1 hr and then the temperature was raised to 60° C. for 4 hr. After cooling down to r.t. 50 ml of sat. NaHCO$_3$ solution were added. The mixture was extracted with 3×50 ml ethyl acetate and the extract was washed with 2×30 ml sat. NaCl solution. The organic layer was dried over K$_2$CO$_3$, filtered and concentrated to a dark yellow syrup. Column chromatography on Silicagel 60 Å using gradient elution with hexane-CH$_2$Cl$_2$-ethyl acetate (95:4:1 to 50:25:25) gave pure 1D-3,6-di-O-benzyl-2-deoxy-fluoro-4,5-O-cycloxylidene-1-O-(p-methoxybenzyl)-myo/scyllo-inositol; 0.5894 g (60%): [α]$_{589}$ −20.46° (c 0.5,CHCl$_3$) MALDI TDF MS m/z 587.19; calc. (M+Na)$^+$ 586; $^1$H NMR (300 MHz, CDCl$_3$) δppm 1.2–1.9 (br,10H), 3.4–3.6 (m, 2H), 3.6–3.7 (m, 1H), 3.7–3.8 (m, 1H), 3.8 (s, 3H), 4.47–4.57 (t, J 8.6 and 8.05, 1H), 4.6–5.00 (m, 6H), 6.8–7.00 (m,2H), 7.51–7.51(m, 12H).

1D-3,6-Di-O-benzyl-2-deoxy-fluoro-1-O-(p-methoxybenzyl)-myo/scyllo-inositol

To a solution of 1D-3,6-di-O-benzyl-2-deoxy-fluoro-4,5-O-cycloxylidene-1-O-(p-methoxybenzyl)-myo/scyllo-inositol (0.566 g ,1.007 mmol) and ethylene glycol (0.11 ml, 1.9 mmol) in 6 ml CH$_2$Cl$_2$-hexane (2:1), 12 mg of p-toluenesulphonic acid monohydrate was added. Reaction mixture was stirred at r.t. for 1 hr, then neutralized with 15 μl triethyl amine and 1 ml sat. NaHCO$_3$ solution. The product was extracted with 3×5 ml CH$_2$Cl$_2$. Organic layer was dried over Na$_2$SO$_4$ and concentrated. Chromatography on Silicagel 60 Å using CHCl$_3$ as eluent gave pure 1D-3, 6-di-O-benzyl-2-deoxy-fluoro-1-O-(p-methoxybenzyl)-myo/scyllo-inositol: 449.4 mg (92.6%). [α]$_{589}$ +9.0° (c 1.0, CHCl$_3$) MALDI TDF MS $^1$H NMR (300 MHz, CDCl$_3$) δppm 2.6 (d, 2H), 3.35 (t, 2H), 3.45 (m, 2H), 3.65 (m, 1H), 3.83 (s, 3H), .4.4–4.6 (ψt, J 2.7 and 6.44, 1H), 4.62–4.85 (m, 4H), 4.87–5.00 (dd, 2H), 6.75–7.00 (d, 2H), 7.18–7.60 (m, 12H).

1D-3,6-Di-O-benzyl-2-deoxy-fluoro-1-O-(p-methoxybenzyl)-myo/scyllo-inositol 4,5-bis-O-dibenzylphosphate To a mixture of 1D-3,6-di-O-benzyl-2-deoxy-fluoro-1-O-(p-methoxybenzyl)-myo/scyllo-inositol (375 mg, 0.78 mmol) and 1H-tetrazole (358 mg, 5.11 mmol) in 5 dry CH$_2$Cl$_2$ was added N,N-diisopropyl dibenzyl phosphoramidite (0.87 ml, 2.6 mmol). The reaction mixture was stirred at r.t. for 10 min. The TLC in CHCl$_3$-diethyl ether (80:20) showed no starting material left (R$_f$=0.175). The mixture was cooled down to −50° C. (CHCl$_3$/liq.N$_2$) and 3-chloroperoxybenzoic acid (60–80% purity, 877 mg, 3.0 mmol) in 10 ml dry CH$_2$Cl$_2$ was added. The resulting solution was stirred at 0° C. for 15 min. The reaction mixture was diluted with 50 ml CH$_2$Cl$_2$, 100 ml 20% Na$_2$SO$_3$ solution was added and stirred at r.t. for 1 hr (until a negative NaI reaction for peroxides is shown). Organic layer was washed with 3×50 ml sat. NaHCO$_3$ solution; 2×20 ml water and 2×25 ml sat. NaCl solution. Combined organic extracts were dried over Na$_2$SO$_4$, filtered and solvent evaporated. Crude reaction product was chromatographed on Silicagel 60 Å eluting with a gradient of CHCl$_3$/diethyl ether (99:1 to 95:5) giving pure 1D-3,6-di-O-benzyl-2-deoxy-fluoro-1-O-(p-methoxybenzyl)-myo/scyllo-inositol 4,5-bis-O-dibenzylphosphate: 702.5 mg (90.1%). [α]$_{589}$ −15.03° (c 0.9, CHCl$_3$) MALDI TDF MS m/z, $^1$H NMR (300 MHz, CDCl$_3$) δppm 1.02–1.34 (dd, 5H), 2.04–2.3 (s, 1H), 3.38–3.9 {m,s, 8H [3.35 (t, 2H)], 3.45 (m, 2H), 3.65 (m, 1H), 3.8 (s, 3H)}, 4.4–4.6 (m, 1H), 4.7–5.3 (m, 14H), 6.6–6.9 (m, 2H), 7.0–7.5 (m, 32H).

1D-3,6-di-O-benzyl-2-deoxy-fluoro-myo/scyllo-inositol 4,5-bis-O-dibenzylphosphate To a 0° C. solution of 1D-3,6-di-O-benzyl-2-deoxy-fluoro-1-O-(p-methoxybenzyl)-myo/scyllo-inositol 4,5-bis-O-dibenzylphosphate (600 mg, 0.5986 mmol) in 6 ml CH$_2$Cl$_2$-H$_2$O(20:1) was added solid 2,3-dichloro-5,6-dicyano-1,4-benzoquinone (DDQ) (540 mg, 2.36 mmol). After 2 hr. the reaction mixture was diluted with cold sat. NaHCO$_3$ solution (200 ml) and extracted with CH$_2$Cl$_2$ (4×50 ml). The combined organic extracts were washed with brine, dried over Na$_2$SO$_4$, evaporated and the residue purified by column chromatography on Silicagel 60 Å with gradient elution with CHCl$_3$-diethyl ether to give 1D-3,6-di-O-benzyl-2-deoxy-fluoro-myo/scyllo-inositol 4,5-bis-O-dibezylphosphate: 387.2 mg (73.3%). [α]$_{589}$ −12.2° (c 0.98, CHCl$_3$) MALDI TDF MS m/z 906.0, calc. (M+Na)$^+$ 905.85.
$^1$H-NMR (300 MHz, CDCl$_3$) δppm 1.2 (s, 2H), 1.56 (s, 6H), 2.78 (s, ½H), 3.38 (ψt, J 1H), 3.35 (m, 1H), 3.77 (m,1H), 4.45–4.58 (m, 4H), 4.6–5.1 (m, 10H), 5.24 (s, 8H), 7.75 (m, 30H).

1D-3,6-di-O-benzyl-1-O-(1',2'-O-dibutyl-sn-glycero-3'-phospho)-2-deoxy-fluoro-myo/scyllo-inositol 4,5-bis-O-dibenzylphosphate To a solution of 1D-3,6-di-O-benzyl-2-deoxy-fluoro-myo/scyllo-inositol 4,5-bis-O-dibezylphosphate of 41.1 mg (0.0466 mmol) (dried excessively over P$_2$O$_5$) in dry pyridine was added triisopropyl-benzene sulphonyl chloride 100 mg (0.33 mmol). After stirring for 15 mins. at r.t. 1,2-dibutyl-sn-glycero-3-phosphate(phosphatidic acid) 34.1 mg (0.12 mmol) was added. After 10 hr. at r.t. reaction mixture was hydrolyzed by diluting with CH$_2$Cl$_2$—H$_2$O (20:1) and leaving at r.t. overnight. After evaporating the solvents to dryness the residue was extracted with anhydrous diethyl ether, which gave the crude reaction product. Purification on Silicagel 60 Å with gradient elution with CHCl$_3$-triethylamine and subsequent chromatography eluting with CHCl$_3$—CH$_3$OH—NH$_4$OH gave the product: 11.5 mg, 21.5%. [α]$_{589}$ +6.22° (c 0.94, CHCl$_3$) MALDI TDF MS m/z; $^1$H NMR (300 MHz, D$_2$O) δppm 0.7–0.8 (br, 3H), 0.95–1.03 (m, 15H), 1.1–1.3 (br, 3H), 1.35–1.5 (ψt, 3H), 2.55 (s, 3H), 2.8–3.0 (d, 1H), 3.3–3.45 (m, 10 or 15H), 3.5–3.66 (m, 3H), 3.7–3.85 (m, 3H), 3.9–4.1 (br, 1H), 4.15–4.3 (br, 1H), 4.35–4.4 (br, 1H), 4.65 (s,); 1H NMR (300 mhz, DMSO) δppm 0.8–0.9 (br, 2H), 1.0–1.1 (m, 5H), 1.12–1.18 (t, 3H), 1.2–1.35 (ψt, 6H), 2.08 (s, 1H), 2.35 (s,), 2.4–2.6 (br,), 2.65 (s,), 2.9–3.2 (dd, 7H), 4.35 (t, 1H), 6.9–7.26 (ψt, 5H).

1D-3,6-Di-O-benzyl-2-deoxy-fluoro-1-O-(1',2'-di-O-palmitoyl-sn-glycero-3'-O-phospho)-myo/scyllo-inositol 4,5-bis-O-dibenzylphosphate To a solution of 1D-3,6-di-O-benzyl-2-deoxy-fluoro-scyllo-inositol 4,5-bis-O-dibezylphosphate (20.8 mg, 0.0236 mmol) in 0.2 ml of dry pyridine was added triisopropyl-benzene sulphonyl chloride (15 mg, 0.0472 mmol). After stirring for 10 mins at r.t., 1,2-dipalmitoyl-sn-3-glycerophosphate (Na salt, 16.5 mg, 0.0246 mmol) was added. After 10 hrs at r.t. reaction mixture was diluted with 2 ml ethanol-free CHCl$_3$ and stirring at r.t. for another 3–4 hrs. Water (1 ml) was added and solvents were removed on a rotary evaporator. The dry residue was extracted with anhydrous diethyl ether (3×5 ml), filtered and the ether was evaporated. The crude product was chromatographed on silicagel 60 Å eluting with a gradient of CHCl$_3$—MeOH—NH$_4$OH (99:1:0.1 to 80:20:2) to afford pure 1D-3,6-di-O-benzyl-2-deoxy-fluoro-1-O-(1', 2'-di-O-palmitoyl-sn-glycero-3'-O-phospho)-myo-inositol 4,5-bis-O-dibenzylphosphate: 10.2 mg, 28.6%. [α]$_{589}$ +10.8° (c 0.5, CHCl$_3$MALDI TDF MS m/z, $^1$H NMR: δppm 0.6–1.0 (m,5H), 1.0–1.4 (s, 2H), 2.2 (br, 4H), 4.0 (br, 1H), 4.4–5.0 (br, 5H), 5.3 (s, 1H), 6.9–7.5 (m, 12H).

1D-2-deoxy-fluoro-1-O-(1',2'-di-O-palmitoyl-sn-glycero-3'-O-phospho)-myo-inositol 4,5-bis-O-phosphate 1D-3,6-di-O-benzyl-2-deoxy-fluoro-1-O-(1', 2'-di-O-palmitoyl-sn-glycero-3'-O-phospho)-myo-inositol 4,5-bis-O-dibenzylphosphate (5.5 mg, 0.0036 mmol) in 2 ml ethanol and 0.5 ml CHCl$_3$ was hydrogenated for 6 hrs using 10 mg Pd-black and H$_2$ gas at 45 psi. After filtering the catalyst and evaporating the solvent, 1D-2-deoxy-fluoro-1-O-(1'2'-di-O-palmitoyl-sn-glycero-3'-O-phospho)-myo-inositol 4,5-bis-O-phosphate (2.4 mg, 67.8%) was obtained. 1H NMR (300 MHz, DMSO-d$_6$) δppm: 0.8–0.9 (m, 10H), 1.0–1.1 (m,16H), 1.15–1.4 (br, 60H), 1.5–1.6 (ψt, 4H), 2.1–2.3 (d,t, 2H (2.35 (ψt, 1H), 2.45–2.55? 2.55–2.6 (t, 4H), 2.6–2.66 (t, 1H), 2.68–2.74 (m, 4H), 2.88 (s, 1H), 3.34–3.42 (m, 18H), 3.5 (d, 1H), 3.98–4.06 (m, 4H), 4.1–4.18 (t, 1H), 5.1 (s, 1H), 7.8 (m, 1H).

1D-2,3,6-Tri-O-benzyl-1-p-methoxybenzyl)-myo-inositol 1D-3,6-Di-O-benzyl-4,5-O-cyclohexylidene-1-(p-methoxybenzyl)-myo-inositol (29 mg, 0.052 mmol) was treated with 1.5 ml DMF, 2 mg (0.05 mmol) NaH (60%, in oil) and 6 μl (0.05 mmol) benzyl bromide at 0–5° C. TLC (hexane-ethyl acetate 70:30) showed reaction was over. Excess NaH was destroyed by adding DH$_2$O at 0–5° C. DMF and water were evaporated. Residue was extracted, evaporated to dryness.

To the crude material, 100 μl CH$_2$Cl$_2$, 20 μl of p-toluenesulfonic acid solution (dissolved in ethylene glycol, 140 mg/4 ml) were added. Reaction was stirred at r.t. for several hours. TLC (CHCl$_3$-MeOH 95:5) showed conversion was finished. Two drops of triethylamine was added. Reaction was diluted, extracted, dried and concentrated. Column chromatography of the crude material eluted with a mixture of CHCl$_3$-MeOH gave pure 1D-2,3,6-tri-O-benzyl-1-(p-methoxybenzyl)-myo-inositol. 21 mg, 70%, [α]$_D$+ 10.79° (c 1.39, CHCl$_3$).

1D-2,3,6-Tri-O-benzyl-1-O-(p-methoxybenzyl)-myo-inositol 4,5-bis-O-dibenzylphosphate To a solution of 1D-2,3,6-tri-O-benzyl-1-O-(p-methoxybenzyl)-myo-inositol (26.7 mg, 0.0468 mmol) in 2 ml CH$_2$Cl$_2$ (dried over P$_2$O$_5$), 1H tetrazole (26.25 mg, 0.37 mmol) and N,N-diisopropyldibenzylphosphoramidite (26.25 mg ,0.37 mmol) were added. Solution was stirred at r.t. for 30 mins. 3-chloroperoxybenzoic acid (71.1 mg, 0.41 mmol) was added at −40° C. Reaction was stirred at 0–5° C. for 15 mins. TLC (hexane-ethyl acetate 60:40) showed reaction was over. 20 ml 20% Na$_2$SO$_3$ solution was added, reaction was stirred for ½ hour. NaI test was checked (negative). Reaction was then extracted with CH$_2$Cl$_2$, washed with saturated NaHCO$_3$ solution, followed by saturated NaCl solution. CH$_2$Cl$_2$ layer was dried and concentrated. Column chromatography of the crude material eluted with a gradient of hexane-CH$_2$Cl$_2$-ethyl acetate gave pure 1D-2,3,6-tri-O-benzyl-1-O-(p-methoxybenzyl)-myo-inositol 4,5-bis-O-dibenzylphosphate. 37 mg, 70% [α]$_D$− 9.37° (c 1.03, CHCl$_3$).

1D-2,3,6-Tri-O-benzyl-myo-inositol 4,5-bis-O-dibenzylphosphate

A mixture of 1D-2,3,6-tri-O-benzyl-1-O-p-methoxybenzyl)-myo-inositol 4,5-bis-O-dibenzylphosphate (30 mg, 0.026 mmol), 1.5 ml CH$_2$Cl$_2$, 1 drop of DH$_2$O and 2,3-dichloro-5,6-dicyano-1,4-benzoquinone (12.5 mg, 0.055 mmol) was stirred at r.t. for 15 mins. TLC (hexane-ethyl-acetate 50:50) showed reaction was complete. Solution was then extracted, washed with cold saturated NaHCO$_3$ solution, followed by cold saturated NaCl solution. CH$_2$Cl$_2$ layer was dried and concentrated. Column chromatography of the crude material with a gradient of hexane-CH$_2$Cl$_2$-ethyl acetate gave pure 1D-2,3,6-Tri-O-benzyl-myo-inositol 4,5-bis-O-dibenzylphosphate. 22 mg, 85% [α]$_D$=−11.01 (c 0.99, CHCl$_3$).

ω-Cbz-aminobutanoic acid

N-aminobutanoic acid (5.06 g, 0.05 mol) was treated with benzyl chloroformate (7.8 ml 0.055 mol) and NaOH solution (2 g in 50 ml $DH_2O$) altenatingly at 0–5° C. in 1 hr. Mixture was stirred at r.t. for 48 hrs. Reaction was extracted with $CHCl_3$ 4×30 ml. Aqueous layer was acidified to PH≈2–3. An oil precipitated and quickly solidified. White solid was filtered out, washed with water several times and dried on a funnel. White precipitates was then dissolved in $CH_2Cl_2$, filtered, dried over $Na_2SO_4$, filtered one more time and evaporated to dryness. 8.98 g, 75%, m.p.: 63–65° C.

1-O-Hexanoyl-2-O-(ω-Cbz-aminobutanoyl)-sn-glycero-3-phosphocholine

Preparation of anhydride: dicyclohexylcarbodi-imide (1.6128 g, 7.82 mmol) was dissolved in 10 ml dry $CCl_4$; ω-Cbz-aminobutanoic acid (3.384 g, 14.26 mmol) was dissolved in a mixture of $CCl_4$ (25 ml) and $CH_2Cl_2$ (20 ml). Dicyclohexylcarbodi-imide solution was pipetted to the ω-Cbz-aminobutanoic acid solution. Mixture was stirred at r.t. for 1 hr until white precipitate appeared and was filtered. Esterification: 1-O-hexanoyl-sn-glycero-3-phosphocholine (1.0114 g, 2.85 mmol) was dissolved in dry $CHCl_3$ (20 ml), dimithylaminopyridine (0.426 g, 2.85 mmol) was added, followed by the anhydride solution prepared earlier. The solution was stirred for a short while before adding dicyclohexylcarbodi-imide (0.654 g, 3.17 mmol) in $CCl_4$ (5 ml). Mixture was stirred at r.t. for 48 hrs. Reaction was then filtered, precipitates were washed with less than 1 ml $CCl_4$. Solvents were evaporated, resulting viscous colorless residue was purified by chromatography on silicagel eluted with $CHCl_3$-MeOH gave 1-O-hexanoyl-2-O-(ω-Cbz-aminobutanoyl)-sn-glycero-3-phosphocholine. 1.3 g, 80%.

1-O-Hexanoyl-2-O-(ω-Cbz-aminobutanoyl)-sn-glycero-3-phosphoric acid

1-O-hexanoyl-2-O-(ω-Cbz-amninobutanoyl)-sn-glycero-3-phosphocholine (0.8063 g, 1.4 mmol) in 15 ml acetate buffer (PH=5.6) was sonicated. 100 ml acetate buffer, phospholipase D (4 mg) and ethanol free ether were added. Mixture was stirred vigorously for 1.5 hrs at 37° C. and white precipitates formed. To the cold (0–5° C.) reaction, a cold solution of $CHCl_3$ (140 ml), MeOH (280 ml) and concentrated HCl(1.2 ml) was added. Reaction was mixed well and aqueous layer was extracted with cold $CHCl_3$ 7×50 ml. Combined organic layer was filtered and evaporated to dryness. 0.68 g, 100%.

1D-1-[1'-O-Hexanoyl-2'-O-(ω-Cbz-aminobutanoyl)-sn-glycero-3'-phospho]-3,6-di-O-benzyl-myo-inositol-4,5-bis-O-dibenzylphosphate To a solution of 1D-3,6-di-O-benzyl-myo-inositol-4,5-bis-O-dibezylphosphate (33.5 mg, 0.038 mmol) (dried excessively over $P_2O_5$) in dry pyridine was added triisopropyl-benzene sulphonyl chloride (34.7 mg, 0.114 mmol). After stirring for 15 mins. at r.t., 1-O-hexanoyl-2-O-(ω-Cbz-aminobutanoyl)-sn-glycero-3-phosphocholine (36.2 mg, 0.076 mmol) was added. After 10 hrs. at r.t. reaction mixture was hydrolyzed by diluting with $CH_2Cl_2$—$H_2O$ (20:1) and leaving at r.t. overnight. After evaporating the solvents to dryness the residue was extracted with anhydrous diethyl ether, which gave the crude reaction product. Purification on Silicagel with gradient elution with $CHCl_3$-triethylamine and subsequent chromatography eluting with $CHCl_3$—$CH_3OH$—$NH_4OH$ gave 1D-1-[1'-O-hexanoyl-2'-O-(ω-Cbz-aminobutanoyl)-sn-glycero-3'-phospho]-3,6-di-O-benzyl-myo-inositol-4,5-bis-O-dibenzylphosphate: 24.7 mg, 48%.

1D-1-[1'-O-Hexanoyl-2'-O-(ω-aminobutanoyl)-sn-glycero-3'-phospho]-myo-inositol-4,5-bis-O-phosphate 1D-1-[1'-O-hexanoyl-2'-O-(ω-Cbz-aminobutanoyl)-sn-glycero-3'-phospho]-3,6-di-O-benzyl-myo-inositol-4,5-bis-O-dibenzylphosphate (24.7 mg, 0.018 mmol) was hydrogenated and recovered and characterized as described for 1D-2-deoxy-fluoro-1-O-(1', 2'-di-O-palmitoyl-sn-glycero-3'-O-phospho)-myo-inositol 4,5-bis-O-phosphate.

LITERATURE CITED

Aneja R. (1974) Biochem. Soc. Trans., 2, 38–41.
S. G. Aneja, A. Parra, C. Stoenescu, W. Xia and R. Aneja (1997) Tetrahedron Lett., 38, 803–806.
Auger K. R., Serunian L. A., Soltoff S. P., Libby P., Cantley L. C. (1989) Cell, 57, 167–175.
Berridge M. J. (1984) Biochem. J., 220, 345.
Bruzik K. S. and Tsai, M-D. (1994) Bioorg. Med. Chem. 2, 49–72.
Carpenter C. L. and Cantley, L. C. (1990) Biochemistry, 29, 11147–56.
Carpenter C. L. and Cantley, L. C. (1996) Biochim. Biophys. Acta, 1288, M 11–M16.
Carpenter, C. L. and Cantley, L. C. Current Opinion in Cell Biology 1996, 8, 153–158.
Chen J., Profit A. A. and Prestwich G. D. (1996) J. Org. Chem. 61, 6305–6312.
Coughlin S. R., Escobedo J. A., Williams, L. T. (1989) Science, 243, 1191–94.
Essen L-O, Perisic O., Cheung R., Katan M. and Williams, R. L. (1996) Nature, 380, 595–602.
Essen L-O, Perisic O., Katan M., Wu, Y., Roberts, M. F. and Williams, R. L. (1997) Biochemistry, 36, 1704–1718.
Gadella T. W. J., Moritz A., Westerman J., and Wirtz K. W. A. (1990) Biochemistry, 29, 3389–3395.
Grobler J. A. and Hurley J. H. (1996) Protein Science 5, 680–686.
Gu Q. M. and Prestwich G. D. (1996) J. Org. Chem. 61, 8642–8647.
Heinz D. W., Ryan M., Bullock T. L., Griffith O. H. (1995) The EMBO J. 14, 3855–3863.
Hendrickson H. S., Hendrickson E. K., Johnson J. L., Khan T. H., and Chial H.J. (1992) Biochemistry, 31, 12169–12172.
Kozikowski A. P, U.S. Pat. No. 5,053,399
Kozikowski A. P., Faug A. H. and Powis G. (1993) U.S. Pat. No. 5,227,508.
Lin G., Bennett F., and Tsai M-D. (1990) Biochemistry, 29, 2747–2757.
Majerus P. W. (1992) Annu. Rev. Biochem., 61,225–250.
Nishizuka Y. (1983) Trends in Biochem. Sc., 8, 13.
Serunian L. A., Haber M. T., Fukui T., Kim J. W., Rhee S. G., Lowenstein J. M., and Cantley, L. (1989) J. Biol. Chem., 264, 17809–17815.
Shashidhar M. S., Volwerk J. J., Griffith O. H., and Keana F. W., (1991) Chem. Phys. Lipids, 60, 101–110.
Volwork J. J., Shasbidhar M. S., Kuppe A., and Griffith O. H. (1 990) Biochemistry, 29, 8056–8060.
Whitman M., Downes C. P., Keeler M., Keller T., Cantley L. (1988) Nature, 332, 644–46.
Yang S. S., Beattie T. R., Durette P. L., Gallagher T. F. and Shen T-Y. (1985) U.S. Pat. No. 4,515,722).

What is claimed is:

1. A phosphoinositide analogue based on di-O-fattyacyl (or alkyl)-sn-glycero-3'-phospho-myo-inositol or di-O-fattyacyl (or alkyl)-sn-glycero-3'-phospho-scyllo-inositol having at least one additional hydroxyl group derivatized as a phosphate, wherein said phosphoinositide analogue incorporates one or more of the following modifying structural features:
   (a) the 2-OH is rendered non-nucleophilic by derivatization or replacement; or
   (b) a reporter group or conjugand is incorporated in the fatty acyl or inositol residue;
wherein the core structure and absolute stereochemistry of the unmodified di-O-fattyacyl (or alkyl)-sn-glycero-3'-phospho-myo-inositol phosphate or di-O-fattyacyl (or alkyl)-sn-glycero-3'-phospho-scyllo-inositol phosphate is maintained in said phosphoinositide analogue.

2. The phosphoinositide analogue of claim 1, wherein said phosphoinositide analogue is a phosphoinositide-(monophosphate) analogue.

3. The phosphoinositide analogue of claim 1, wherein said phosphoinositide analogue is a phosphoinositide-(diphosphate) analogue.

4. The phosphoinositide analogue of claim 3, wherein said phosphoinositide analogue is a PtdIns(4,5)P$_2$ analogue.

5. The phosphoinositide analogue of claim 1, wherein said phosphoinositide analogue is a phosphoinositide-(polyphosphate) analogue.

6. The phosphoinositide analogue of claim 1, wherein the 2-OH is rendered non-nucleophilic by derivatization or replacement.

7. The phosphoinositide analogue of claim 6, wherein the 2-OH is rendered non-nucleophilic by derivatization.

8. The phosphoinositide analogue of claim 7, wherein the 2-OH is rendered non-nucleophilic by derivatization to form a 2-OCOR or 2-OR phosphoinositide analogue, wherein R is alkyl, substituted alkyl or alkenyl.

9. The phosphoinositide analogue of claim 8, wherein the 2-OH is rendered non-nucleophilic by derivatization to form 2-OAc.

10. The phosphoinositide analogue of claim 8, wherein the 2-OH is rendered non-nucleophilic by derivatization to form a 2-OCOR or 2-OR phosphoinositide analogue, wherein R is $CH_3$.

11. The phosphoinositide analogue of claim 8, wherein the 2-OH is rendered non-nucleophilic by derivatization to form a 2-OCOR or 2-OR phosphoinositide analogue, wherein R is ω-amino-alkyl.

12. The phosphoinositide analogue of claim 8, wherein the 2-OH is rendered non-nucleophilic by derivatization to form a 2-OCOR or 2-OR phosphoinositide analogue, wherein R is N-substituted-ω-amino-alkyl.

13. The phosphoinositide analogue of claim 8, wherein the 2-OH is rendered non-nucleophilic by derivatization to form a 2-OCOR or 2-OR phosphoinositide analogue, wherein R is N,N-disubstituted-ω-amino-alkyl.

14. The phosphoinositide analogue of claim 6, wherein the 2-OH is rendered non-nucleophilic by replacement.

15. The phosphoinositide analogue of claim 14, wherein the 2-OH is rendered non-nucleophilic by replacement to form the 2-deoxyhalo or 2-dideoxyhalo phosphoinositide analogue.

16. The phosphoinositide analogue of claim 15, wherein the 2-OH is rendered non-nucleophilic by replacement to form the 2-deoxyfluoro phosphoinositide analogue.

17. The phosphoinositide analogue of claim 1, wherein a reporter group or conjugand is incorporated in the fatty acyl or inositol residue.

18. The phosphoinositide analogue of claim 17, wherein a reporter group is incorporated.

19. The phosphoinositide analogue of claim 18, wherein the reporter group is a photoaffinity reporter group.

20. The phosphoinositide analogue of claim 18, wherein the reporter group is a fluorescent reporter group.

21. The phosphoinositide analogue of claim 18, wherein the reporter group is a spin probe reporter group.

22. The phosphoinositide analogue of claim 18, wherein the reporter group is a radioactive label reporter group.

23. The phosphoinositide analogue of claim 18, wherein the reporter group is a stable isotope label reporter group.

24. The phosphoinositide analogue of claim 17, wherein a conjugand is incorporated.

25. The phosphoinositide analogue of claim 24, wherein the conjugand is alkyl-C=O, (ω-$NH_2$-alkyl-C=O, ω-$NH_2$-alkyl, ω-thio-(alkyl-C=O) or ω-thio-alkyl.

26. The phosphoinositide analogue of claim 24, wherein the conjugand is suitable for linking the phosphoinositide analogue to a polymer.

27. The phosphoinositide analogue of claim 24, wherein the conjugand is suitable for linking the phosphoinositide analogue to a chromatographic matrix.

28. The phosphoinositide analogue of claim 24, wherein the conjugand is suitable for linking the phosphoinositide analogue to a gold surface.

29. The phosphoinositide analogue of claim 24, wherein the conjugand is suitable for linking the phosphoinositide analogue to a reporter group.

30. The phosphoinositide analogue of claim 1, wherein one or both glycerol esters are replaced by ether bonds.

31. A selectively O-protected phosphoinositide analogue obtained as a phosphodiester intermediate formed by the reaction of a selectively protected myo-inositol phosphate or scyllo-inositol phosphate and an sn-3-phosphatidic acid or glycero-ether analogue, wherein the said O-protected phosphoinositide analogue has the structure:

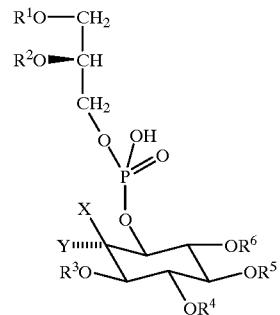

wherein at least one of $R^3$, $R^4$, $R^5$, $R^6$ is P(=O)(O-protecting group)$_2$,
and wherein:
   (a) X=F, Cl, Br, OC(=O)R, OR, or P(=O)(O-protecting group)$_2$, and Y=H; or X=Y=H; or
   (b) X=H, and Y F, Cl, Br, OC(=O)R, OR, or P(=O)(O-protecting group)$_2$; or
   (c) X=Y=F or (=O);
      where R=alklyl, especially methyl or ethyl, alkenyl, alkynyl, ω-aminoalkyl, N-substituted-ω-aminoalkyl or N,N-disubstituted-ω-aminoalkyl;
and wherein
   (d) $R^1$=RC(=O) or R, $R^2$=R'C(=O) or R'
      where R, R'=alkyl or alkenyl;
and wherein:

(e) $R^3$=H, or P(=O)(O-protecting group)$_2$,
(f) $R^4$=H, or P(=O)(O-protecting group)$_2$,
(g) $R^5$=H, or P(=O)(O-protecting group)$_2$,
(h) $R^6$=H, P(=O)(O-protecting group)$_2$, ω-aminoalkyl, ω-aminoalkenyl, ω-sulfhydrylalkyl, ω-carboxyalkyl, ω-(4-azidosalicylamido)-alkyl, alkyl-aminofluorophor, alkyl-amidofluorophor, or alkyl-fluorophor.

32. The phosphoinositide analogue of claim 1, wherein:
(a) the 2-OH is rendered non-nucleophilic by derivatization or replacement; and
(b) a reporter group or conjugand is incorporated in the fatty acyl or inositol residue;
wherein the core structure and absolute stereochemistry of the unmodified di-O-fattyacyl (or alkyl)-sn-glycero-3'-phospho-myo-inositol phosphate or di-O-fattyacyl (or alkyl)-sn-glycero-3'-phospho-scyllo-inositol phosphate is maintained in said phosphoinositide analogue.

33. A phosphoinositide analogue based on di-O-fattyacyl (or alkyl)-sn-glycero-3'-phospho-myo-inositol or di-O-fattyacyl (or alkyl)-sn-glycero-3'-phospho-scyllo-inositol having at least one additional hydroxyl group derivatized as a phosphate, wherein the 2-OH is rendered non-nucleophilic by derivatization or replacement and wherein the core structure and absolute stereochemistry of the unmodified di-O-fattyacyl (or alkyl)-sn-glycero-3'-phospho-myo-inositol phosphate or di-O-fattyacyl (or alkyl)-sn-glycero-3'-phospho-scyllo-inositol phosphate is maintained in said phosphoinositide analogue.

34. The phosphoinositide analogue of claim 1, wherein said phosphoinositide analogue is based on di-O-fattyacyl (or alkyl)-sn-glycero-3'-phospho-myo-inositol phosphate.

35. The phosphoinositide analogue of claim 1, wherein said phosphoinositide analogue is based on di-O-fattyacyl (or alkyl)-sn-glycero-3'-phospho-scyllo-inositol phosphate.

36. A selectively O-protected phosphoinositide analogue obtained as a phosphodiester intermediate formed by the reaction of a selectively protected myo-inositol phosphate or scyllo-inositol phosphate and an sn-3-phosphatidic acid or glycero ether analogue, wherein the said O-protected phosphoinositide analogue has the structure:

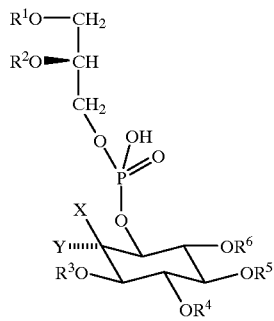

wherein at least one of $R^3$, $R^4$, $R^5$, $R^6$ is P(=O)(O-protecting group)$_2$,
and wherein
(a) X=OH, and Y=H; or X=H, and Y=OH;
and wherein
(b) $R^1$=RC(=O) or R, $R^2$=R'C(=O) or R'
where R=alkyl, alkenyl, alkynyl, R'=ω-aminoalkyl, ω-(substitutedamino)-alkyl, ω-aminoalkenyl, ω-sulfhydrylalkyl, ω-carboxyalkyl, ω-(4-azidosalicylamido)-alkyl, ω-(substitutedamido)-alkyl, alkyl-aminofluorophor, alkyl-amidofluorophor, alkyl-fluorophor, hydroxylalkyl, or ketoalkyl; or where R'=alkyl, alkenyl, alkynyl, R=ω-aminoalkyl, ω-(substitutedamino)-alkyl, ω-aminoalkenyl, ω-sulfhydrylalkyl, ω-carboxyalkyl, ω-(4-azidosalicylamido)-alkyl, ω-(substitutedamido)-alkyl, alkyl-aminofluorophor, alkyl-amidofluorophor, alkyl-fluorophor, hydroxylalkyl, or ketoalkyl; or where R=R', except when R=R'=alkyl;
and wherein
(c) $R^3$=H, or P(=O)(O-protecting group)$_2$,
(d) $R^4$=H, or P(=O)(O-protecting group)$_2$,
(e) $R^5$=H, or P(=O)(O-protecting group)$_2$,
(f) $R^6$=H, P(=O)(O-protecting group)$_2$, ω-aminoalkyl, ω-aminoalkenyl, ω-sulfhydrylalkyl, ω-carboxyalkyl, ω-(4-azidosalicylamido)-alkyl, alkyl-aminofluorophor, alkyl-amidofluorophor, or alkyl-fluorophor.

37. A selectively O-protected phosphoinositide analogue obtained as a phosphodiester intermediate formed by the reaction of a selectively protected myo-inositol phosphate or scyllo-inositol phosphate and an sn-3-phosphatidic acid or glycero ether analogue, wherein the said O-protected phosphoinositide analogue has the structure:

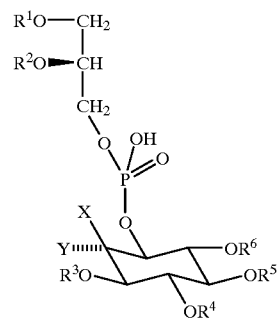

wherein at least one of $R^3$, $R^4$, $R^5$, $R^6$ is P(=O)(O-protecting group)$_2$,
and wherein
(a) X=F, Cl, Br, OC(=O)R, OR, or P(=O)(O-protecting group)$_2$, and Y=H; or X=Y=H; or
(b) X=H, and Y=F, Cl, Br, OC(=O)R, OR, or P(=O)(O-protecting group)$_2$, or
(c) X=Y=F or (=O);
where R=alkyl, especially methyl or ethyl, alkenyl, alkynyl, ω-aminoalkyl, N-substituted-ω-aminoalkyl or N,N-disubstituted-ωaminoalkyl;
and wherein
(d) R'=RC(=O) or R, $R^2$=R'C(=O) or R'
where R=alkyl, alkenyl, alkynyl, R'=ω-aminoalkyl, ω-(substitutedamino)-alkyl, ω-aminoalkenyl, ω-sulfhydrylalkyl, ω-carboxyalkyl, ω-(4-azidosalicylamido)-alkyl, ω-(substitutedamido)-alkyl, alkyl-aminofluorophor, alkyl-amidofluorophor, alkyl-fluorophor, hydroxylalkyl, or ketoalkyl; or where R'=alkyl, alkenyl, alkynyl, R=ω-aminoalkyl, ω-(substitutedamino)-alkyl, ω-aminoalkenyl, ω-sulfhydrylalkyl, ω-carboxyalkyl, ω-(4-azidosalicylamido)-alkyl, ω-substitutedamido)-alkyl, alkyl-aminofluorophor, alkyl-amidofluorophor, alkyl-fluorophor, hydroxylalkyl, or ketoalkyl; or where R=R';
and wherein
(e) $R^3$=H, or P(=O)(O-protecting group)$_2$, (f) $R^4$=H, or P(=O)(O-protecting group)$_2$, (g) $R^5$=H, or P(=O)(O-protecting group)$_2$, (h) $R^6$=H, P(=O)(O-protecting group)$_2$, ω-aminoalkyl, ω-aminoalkenyl, ω-sulfhydrylalkyl, ω-carboxyalkyl, ω-(4-azidosalicylamido)-alkyl, alkyl-aminofluorophor, alkyl-amidofluorophor, or alkyl-fluorophor.

38. A phosphoinositide analogue based on phosphatidylinositolphosphate, wherein the 2-OH is rendered non-nucleophilic by derivatization or replacement or wherein a reporter group or conjugand is incorporated in the fatty acyl or inositol residue; wherein the core structure and absolute stereochemistry of the unmodified phosphatidylinositolphosphate is maintained in said phosphoinositide analogue; and wherein said phosphoinositide analogue has the structure:

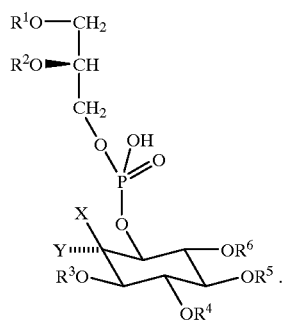

wherein at least one of $R^3$, $R^4$, $R^5$, $R^6$ is P(=O)(OH)$_2$, and wherein (a) X=F, Cl, Br, OC(=O)R, OR, or OP(=O)(OH)$_2$, and Y=H; or X=Y=H; or (b) X=H, and Y=F, Cl, Br, OC(=O)R, OR, or OP(=O)(OH)$_2$; or (c) X=Y=F or (=O);

where R=alkyl, especially methyl or ethyl, alkenyl, alkynyl, ω-aminoalkyl, N-substituted-ω-aminoalkyl or N,N-disubstituted-ω-aminoalkyl;

and wherein (d) $R^1$=RC(=O) or R, $R^2$=R'C(=O) or R'
where R, R'=alkyl or alkenyl;

and wherein (e) $R^3$=H, or P(=O)(OH)$_2$ (f) $R^4$=H, or P(=O)(OH)$_2$ (g) $R^5$=H, or P(=O)(OH)$_2$ (h) $R^6$=H, P(=O)(OH)$_2$, ω-aminoalkyl, ω-aminoalkenyl, ω-sulfhydrylalkyl, ω-carboxyalkyl, ω-(4-azidosalicylamido)-alkyl, alkyl-aminofluorophor, alkyl-amidofluorophor, or alkyl-fluorophor.

39. A phosphoinositide analogue based on phosphatidylinositolphosphate, wherein the 2-OH is rendered non-nucleophilic by derivatization or replacement or wherein a reporter group or conjugand is incorporated in the fatty acyl or inositol residue; wherein the core structure and absolute stereochemistry of the unmodified phosphatidylinositolphosphate is maintained in said phosphoinositide analogue; and wherein said phosphoinositide analogue has the structure:

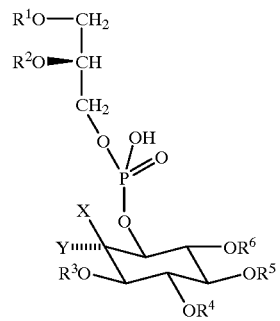

wherein at least one of $R^3$, $R^4$, $R^5$, $R^6$ is P(=O)(OH)$_2$, and wherein (a) X=OH, and Y=H; or X=H, and Y=OH;

and wherein (b) $R^1$=RC(=O) or R, $R^2$=R'C(=O) or R'
where R=alkyl, alkenyl, alkyl, R'=ω-aminoalkyl, ω-(substitutedamino)-alkyl, ω-aminoalkenyl, ω-sulfhydrylalkyl, ω-carboxyalkyl, ω-(4-azidosalicylamido) alkyl, ω-(substitutedamido)-alkyl, alkyl-aminofluorophor, alkyl-amidofluorophor, alkynyl, R=ω-aminoalkyl, ω-(substitutedamino)-alkyl, ω-aminoalkenyl, ω-sulfhydrylalkyl, ω-carboxyalkyl, ω(4-azidosalicylamido)-alkyl, ω-(substitutedamido)-alkyl, alkyl-aminofluorophor, alkyl-amidofluorophor, alkyl-fluorophor, hydroxylalkyl, or ketoalkyl; or where R=R', except when R=R'=alkyl;

and wherein (c) $R^3$=H, or P(=O)(OH)$_2$ (d) $R^4$=H, or P(=O)(OH)$_2$ (e) $R^5$=H, or P(=O)(OH)$_2$ (f) $R^6$=H, P(=O)(OH)$_2$, ω-aminoalkyl, ω-aminoalkenyl, ω-sulfhydrylalkyl, ω-carboxyalkyl, ω-(4-azidosalicylamido)-alkyl, alkyl-aminofluorophor, alkyl-amidofluorophor, or alkyl-fluorophor.

40. A phosphoinositide analogue based on phosphatidylinositolphosphate, wherein the 2-OH is rendered non-nucleophilic by derivatization or replacement and a reporter group or conjugand is incorporated in the fatty acyl or inositol residue; wherein the core structure and absolute stereochemistry of the unmodified phosphatidylinositolphosphate is maintained in said phosphoinositide analogue; and wherein said phosphoinositide analogue has the structure:

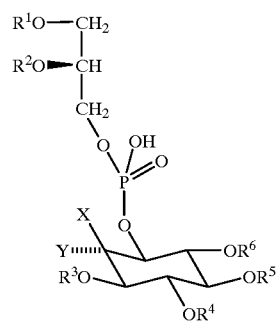

wherein at least one of $R^3$, $R^4$, $R^5$, $R^6$ is P(=O)(OH)$_2$, and wherein (a) X=F, Cl, Br, OC(=O)R, OR, or OP(=O)(OH)$_2$, and Y=H; or X=Y=H; or (b) X=H, and Y=F, Cl, Br, OC(=O)R, OR, or OP(=O)(OH)$_2$; or (c) X=Y=F or (=O);

where R=alkyl, especially methyl or ethyl, alkenyl, alkynyl, ω-aminoalkyl, N-substituted-ω-aminoalkyl or N,N-disubstituted-ω-aminoalkyl;

and wherein (d) $R^1$=RC(=O) or R, $R^2$=R'C(=O) or R' where R=alkyl, alkenyl, alkynyl, R'=ω-aminoalkyl, ω-(substitutedamino)-alkyl, ω-aminoalkenyl, ω-sulfhydrylalkyl, ω-carboxyalkyl, ω-(4-azidosalicylamido)-alkyl, ω-(substitutedamido)-alkyl, alkyl-aminofluorophor, alkyl-amidofluorophor, alkyl-fluorophor, hydroxylalkyl, or ketoalkyl; or where R'=alkyl, alkenyl, alkynyl, R=ω-aminoalkyl, ω-(substitutedamino)-alkyl, ω-aminoalkenyl, ω-sulfhydrylalkyl, ω-carboxyalkyl, ω-(4-azidosalicylamido)-alkyl, ω-(substitutedamido)-alkyl, alkyl-aminofluorophor, alkyl-amidofluorophor, alkyl-fluorophor, hydroxylalkyl, or ketoalkyl; or where R=R';

and wherein (e) $R^3$=H, or P(=O)(OH)$_2$ (f) $R^4$=H, or P(=O)(OH)$_2$ (g) $R^5$=H, or P(=O)(OH)$_2$ (h) $R^6$=H, P(=O)(OH)$_2$, ω-aminoalkyl, ω-aminoalkenyl, ω-sulfhydrylalkyl, ω-carboxyalkyl, ω-(4-azidosalicylamido)-alkyl, alkyl-aminofluorophor, alkyl-amidofluorophor, or alkyl-fluorophor.

41. Matched pairs of the 2-modified phosphatidylinositol-phosphates of claim 38, and the corresponding phosphatidylinositol-phosphate structure lacking the 2-modification, wherein X=OH and Y=H, or X=H and Y=OH.

42. The phosphoinositide analogue of claim 1, wherein said phosphoinositide analogue has the structure:

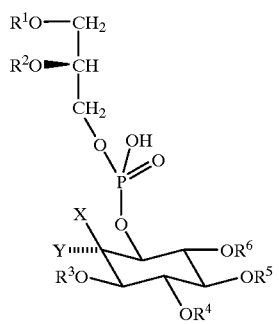

wherein at least one of $R^3$, $R^4$, $R^5$, $R^6$ is P(=O)(OH)$_2$, and wherein (a) X=OH, and Y=H; or X=H, and Y=OH and wherein (b) R'=RC(=O) or R, $R^2$=R'C(=O) or R' where R=alkyl, alkenyl, alkynyl, R'=ω-aminoalkyl, ω-(substitutedamino)-alkyl, ω-aminoalkenyl, ω-sulfhydrylalkyl, ω-carboxyalkyl, ω-(4-azidosalicylamido)-alkyl, ω-substitutedamido)-alkyl, alkyl-aminofluorophor, alkyl-amidofluorophor, alkyl-fluorophor, hydroxylalkyl, or ketoalkyl; or where R'=alkyl, alkenyl, alkynyl, R=ω-aminoalkyl, ω-(substitutedamino)-alkyl, ω-aminoalkenyl, ω-sulfhydrylalkyl, ω-carboxyalkyl, ω(4-azidosalicylamido)-alkyl, ω-(substitutedamido)-alkyl, alkyl-aminofluorophor, alkyl-amidofluorophor, hydroxylalkyl, or ketoalkyl;

and wherein (c) $R^3$=H, or P(=O)(OH)$_2$ (d) $R^4$=H, or P(=O)(OH)$_2$ (e) $R^5$=H, or P(=O)(OH)$_2$ (f) $R^6$=H, P(=O)(OH)$_2$, ω-aminoalkyl, ω-aminoalkenyl, ω-sulfhydrylalkyl, ω-carboxyalkyl, ω-(4-azidosalicylamido)-alkyl, alkyl-aminofluorophor, alkyl-amidofluorophor, or alkyl-fluorophor.

43. A phosphoinositide analogue based on di-O-fattyacyl (or alkyl)-sn-glycero-3'-phospho-myo-inositol or di-O-fattyacyl (or alkyl)-sn-glycero-3'-phospho-scyllo-inositol having at least one additional hydroxyl group derivatized as a phosphate, wherein said phosphoinositide analogue incorporates one or more of the following modifying structural features:

(a) the 2-OH is rendered non-nucleophilic by derivatization or replacement; or (b) a conjugand suitable for linking to a reporter group, polymer, chromatographic matrix, or gold surface is incorporated in the fattyacyl or inositol residue; wherein said conjugand is selected from the group consisting of ω-aminoalkyl, ω-(substitutedamino)-alkyl, ω-aminoalkenyl, ω-sulfhydrylalkyl, ω-carboxyalkyl, hydroxylalkyl and ketoalkyl, and wherein the amino, substitutedamino, sulfhydryl, carboxyl, hydroxyl and keto functions are free and unsubstituted, or are covalently linked to a reporter group;

wherein the core structure and absolute stereochemistry of the unmodified di-O-fattyacyl (or alkyl)-sn-glycero-3'-phospho-myo-inositol phosphate or di-O-fattyacyl (or alkyl)-sn-glycero-3'-phospho-scyllo-inositol phosphate is maintained in said phosphoinositide analogue.

* * * * *

UNITED STATES PATENT AND TRADEMARK OFFICE
CERTIFICATE OF CORRECTION

PATENT NO.   : 6,384,260 B1
DATED        : May 7, 2002
INVENTOR(S)  : Rajindra Aneja It is certified that error appears in the above-identified patent and that said Letters Patent is hereby corrected as shown below:

Columns 13-20,
Claims 1, 31, 32, 33, 34, 36, 37 and 43, at each instance, please delete "myo" and insert -- *myo* -- therefor.
In claims 1, 31, 32, 33, 34, 35 and 43, at each instance, please delete "-sn-" and insert -- *sn-* -- therefor.
In claims 1, 32, 33, 34, 35 and 43, at each instance, please delete "-O-" and insert -- *-O-* -- therefor.
In claims 31, 32, 33, 35, 36, 37 and 43, at each instance, please delete "scyllo" and insert -- *scyllo* -- therefor.

Column 13,
Line 39, please delete "OAc" and insert -- *O*Ac -- therefor.

Columns 14-16,
In claims 31, 36 and 37, at each instance, please delete "O-" and insert -- *O-* -- therefor.
Line 58, please delete "Y F" and insert -- Y = F -- therefor.

Columns 15-16,
Claims 36 and 37, at each instance, please delete "sn-" and insert -- *sn-* -- therefor.

Column 16,
Line 50, please delete "ωaminoalkyl" and insert -- ω-aminoalkyl -- therefor.
Line 63, please delete "ω-substitutedamino)" and insert -- ω-(substitutedamido) -- therefor.

Column 18,
Line 21, please delete "alkenyl, alky" and insert -- alkenyl, alkynyl -- therefor.
Line 26, between the words "aminofluorophor, alkynyl" please insert the following -- alkyl-fluorophor, hydroxylalkyl, or ketoalkyl; or where R' = alkyl, alkenyl, --.

UNITED STATES PATENT AND TRADEMARK OFFICE
CERTIFICATE OF CORRECTION

PATENT NO.   : 6,384,260 B1
DATED        : May 7, 2002
INVENTOR(S)  : Rajindra Aneja It is certified that error appears in the above-identified patent and that said Letters Patent is hereby corrected as shown below:

<u>Column 20,</u>
Line 4, please delete "R'" and insert -- $R^1$ -- therefor.

Signed and Sealed this

Seventeenth Day of September, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 6,384,260 B1
DATED : May 7, 2002
INVENTOR(S) : Rajindra Aneja

It is certified that error appears in the above-identified patent and that said Letters Patent is hereby corrected as shown below:

<u>Title page,</u>
Item [56], OTHER PUBLICATIONS, "Chen et al.," reference, delete "3,45" and insert -- 3,4,5 -- therefor.

<u>Column 1,</u>
Line 8, delete "finds" and insert -- funds -- therefor.
Line 10, after "NIH-GM51138", add -- and Grant No. NIH-GM49594 and NIH-CA57107 --.
Line 31, delete "(PtdIns(4,5)P)" and insert -- (PtdIns(4,5)$P_2$) -- therefor.
Line 34, delete "($P_3$)" and insert -- ($IP_3$) -- therefor.
Line 36, delete "Ca:" and insert -- Ca++ -- therefor.
Line 43, delete "on coproteins" and insert -- oncoproteins -- therefor.
Line 50, delete "Majerms" and insert -- Majerus -- therefor.
Line 62, delete "PtdIns(4,5)$_2$" and insert -- PtdIns(4,5)$P_2$ -- therefor.

<u>Column 2,</u>
Line 14, delete "art (Yang et al., U.S." and insert -- art, Yang et al. (U.S. -- therefor.

<u>Column 3,</u>
Line 12, delete "(ω(-" and insert -- (ω- -- therefor.

<u>Column 4,</u>
Line 27, delete "PI-PLCd1" and insert -- PI-PLCδ1 -- therefor.
Line 30, delete "of".
Line 63, delete "(4,5)" and insert -- (4,5)$P_2$ -- therefor.

<u>Column 5,</u>
Line 12, delete "R.T" and insert -- r.t. -- therefor.
Line 46, delete "bezylaminoalkyl" and insert -- benzylaminoalkyl -- therefor.

<u>Column 6,</u>
Line 12, delete "10 mg" and insert -- 10 $\mu$g -- therefor.

<u>Column 9,</u>
Line 39, delete "scyllo-inositol" and insert -- myo/scyllo-inositol -- therefore.
Line 39, delete "dibezylphosphate" and insert -- dibenzylphosphate -- therefor.
Lines 54, 60 and 63, delete "myo-inositol" and insert -- myo/scyllo-inositol -- therefor.

<u>Column 10,</u>
Line 1, delete "myo-inositol" and insert -- myo/scyllo-inositol -- therefor.

UNITED STATES PATENT AND TRADEMARK OFFICE
CERTIFICATE OF CORRECTION

PATENT NO.   : 6,384,260 B1
DATED        : May 7, 2002
INVENTOR(S)  : Rajindra Aneja It is certified that error appears in the above-identified patent and that said Letters Patent is hereby corrected as shown below:

<u>Column 11,</u>
Line 25, delete "dimithylaminopryridine" and insert -- dimethylaminopyridine -- therefor.
Line 55, delete "dibezylphosphate" and insert -- dibenzylphosphate -- therefor.

Signed and Sealed this

Twenty-sixth Day of August, 2003

JAMES E. ROGAN
*Director of the United States Patent and Trademark Office*

UNITED STATES PATENT AND TRADEMARK OFFICE
CERTIFICATE OF CORRECTION

| | |
|---|---|
| PATENT NO. | : 6,384,260 B1 |
| APPLICATION NO. | : 09/826396 |
| DATED | : May 7, 2002 |
| INVENTOR(S) | : Rajindra Aneja |

It is certified that error appears in the above-identified patent and that said Letters Patent is hereby corrected as shown below:

Title page, Item [56] Other Publication, column 2, line 3, delete "3,45" and insert --3,4,5-- therefor.
In column 1, line 8, delete "finds" and insert --funds-- therefor.
In column 1, line 10, after "NIH-GM51138", add --and Grant No. NIH-GM49594 and NIH-CA57107--.
In column 1, line 31, delete "(PtdIns(4,5)P)" and insert --(PtdIns(4,5)$P_2$)-- therefor.
In column 1, line 34, delete "($P_3$)" and insert --($IP_3$)-- therefor.
In column 1, line 36, delete "Ca:" and insert --Ca++-- therefor.
In column 1, line 43, delete "on coproteins" and insert --oncoproteins-- therefor.
In column 1, line 50, delete "Majerms" and insert --Majerus-- therefor.
In column 1, line 62, delete "PtdIns(4,5)$_2$" and insert --PtdIns(4,5)$P_2$-- therefor.
In column 2, line 14, delete "art (Yang et al., U.S." and insert --art, Yang et al. (U.S.-- therefor.
In column 3, line 12, delete "(ω(-" and insert --(ω- -- therefor.
In column 4, line 27, delete "PI-PLCd1" and insert --PI-PLCδ1-- therefor.
In column 4, line 30, delete "of".
In column 4, line 63, delete "(4,5)" and insert --(4,5)$P_2$-- therefor.
In column 5, line 12, delete "R.T" and insert --r.t.-- therefor.
In column 5, line 46, delete "bezylaminoalkyl" and insert --benzylaminoalkyl-- therefor.
In column 6, line 12, delete "10 mg" and insert --10 μg-- therefor.
In column 9, line 39, delete "scyllo-inositol" and insert --myo/scyllo-inositol-- therefore.
In column 9, line 39, delete "dibezylphosphate" and insert --dibenzylphosphate-- therefor.
In column 9, line 54, delete "myo-inositol" and insert --myo/scyllo-inositol-- therefor.
In column 9, line 60, delete "myo-inositol" and insert --myo/scyllo-inositol-- therefor.

UNITED STATES PATENT AND TRADEMARK OFFICE
CERTIFICATE OF CORRECTION

PATENT NO. : 6,384,260 B1
APPLICATION NO. : 09/826396
DATED : May 7, 2002
INVENTOR(S) : Rajindra Aneja It is certified that error appears in the above-identified patent and that said Letters Patent is hereby corrected as shown below:

In column 9, line 63, delete "myo-inositol" and insert --myo/scyllo-inositol-- therefor.
In column 10, line 1, delete "myo-inositol" and insert --myo/scyllo-inositol-- therefor.
In column 11, line 25, delete "dimithylaminopryridine" and insert --dimethylaminopyridine-- therefor.
In column 11, line 55, delete "dibezylphosphate" and insert --dibenzylphosphate-- therefor.

Signed and Sealed this

Twenty-sixth Day of May, 2009

JOHN DOLL
*Acting Director of the United States Patent and Trademark Office*

UNITED STATES PATENT AND TRADEMARK OFFICE
CERTIFICATE OF CORRECTION

| | |
|---|---|
| PATENT NO. | : 6,384,260 B1 |
| APPLICATION NO. | : 09/826396 |
| DATED | : May 7, 2002 |
| INVENTOR(S) | : Rajindra Aneja |

It is certified that error appears in the above-identified patent and that said Letters Patent is hereby corrected as shown below:

Title page Item [56], column 2, line 3, delete "3,45" and insert --3,4,5-- therefor.
In column 1, line 8, delete "finds" and insert --funds-- therefor.
In column 1, line 10, after "NIH-GM51138", add --and Grant No. NIH-GM49594 and NIH-CA57107--.
In column 1, line 31, delete "(PtdIns(4,5)P)" and insert --(PtdIns(4,5)$P_2$)-- therefor.
In column 1, line 34, delete "($P_3$)" and insert --($IP_3$)-- therefor.
In column 1, line 36, delete "Ca:" and insert --Ca++-- therefor.
In column 1, line 43, delete "on coproteins" and insert --oncoproteins-- therefor.
In column 1, line 50, delete "Majerms" and insert --Majerus-- therefor.
In column 1, line 62, delete "PtdIns(4,5)$_2$" and insert --PtdIns(4,5)$P_2$-- therefor.
In column 2, line 14, delete "art (Yang et al., U.S." and insert --art, Yang et al. (U.S.-- therefor.
In column 3, line 12, delete "($\omega$(-" and insert --($\omega$- -- therefor.
In column 4, line 27, delete "PI-PLCd1" and insert --PI-PLC$\delta$1-- therefor.
In column 4, line 30, delete "of".
In column 4, line 63, delete "(4,5)" and insert --(4,5)$P_2$-- therefor.
In column 5, line 12, delete "R.T" and insert --r.t.-- therefor.
In column 5, line 46, delete "bezylaminoalkyl" and insert --benzylaminoalkyl-- therefor.
In column 6, line 12, delete "10 mg" and insert --10 μg-- therefor.
In column 9, line 39, delete "scyllo-inositol" and insert --myo/scyllo-inositol-- therefor.
In column 9, line 39, delete "dibezylphosphate" and insert --dibenzylphosphate-- therefor.
In column 9, line 54, delete "myo-inositol" and insert --myo/scyllo-inositol-- therefor.
In column 9, line 60, delete "myo-inositol" and insert --myo/scyllo-inositol-- therefor.
In column 9, line 63, delete "myo-inositol" and insert --myo/scyllo-inositol-- therefor.
In column 10, line 1, delete "myo-inositol" and insert --myo/scyllo-inositol-- therefor.

UNITED STATES PATENT AND TRADEMARK OFFICE
CERTIFICATE OF CORRECTION

PATENT NO. : 6,384,260 B1
APPLICATION NO. : 09/826396
DATED : May 7, 2002
INVENTOR(S) : Rajindra Aneja It is certified that error appears in the above-identified patent and that said Letters Patent is hereby corrected as shown below:

In column 11, line 25, delete "dimithylaminopryridine" and insert --dimethylaminopyridine-- therefor.
In column 11, line 55, delete "dibezylphosphate" and insert --dibenzylphosphate-- therefor.

Signed and Sealed this

Second Day of June, 2009

JOHN DOLL
*Acting Director of the United States Patent and Trademark Office*

(12) EX PARTE REEXAMINATION CERTIFICATE (7688th)
United States Patent
Aneja

(10) Number: US 6,384,260 C1
(45) Certificate Issued: Aug. 17, 2010

(54) MOLECULAR PROBES AND MODULATORS FOR PI-PLC AND PI 3-KINASE

(75) Inventor: Rajindra Aneja, Ithaca, NY (US)

(73) Assignee: Nutrimed Biotech, Ithaca, NY (US)

Reexamination Request:
No. 90/009,257, Aug. 14, 2008

Reexamination Certificate for:
Patent No.: 6,384,260
Issued: May 7, 2002
Appl. No.: 09/826,396
Filed: Apr. 3, 2001

Certificate of Correction issued Sep. 17, 2002.

Certificate of Correction issued Aug. 26, 2003.

Certificate of Correction issued May 26, 2009.

Certificate of Correction issued Jun. 2, 2009.

Related U.S. Application Data

(63) Continuation of application No. 08/872,222, filed on Jun. 10, 1997, now Pat. No. 6,232,486.
(60) Provisional application No. 60/019,651, filed on Jun. 11, 1996.

(51) Int. Cl.
  *C07F 9/00* (2006.01)
  *C07F 9/117* (2006.01)
  *C07F 9/10* (2006.01)

(52) U.S. Cl. .................. 558/160; 558/161; 558/179; 558/180; 558/186

(58) Field of Classification Search .................. None
  See application file for complete search history.

(56) References Cited

PUBLICATIONS

Dreef, Synthesis of 1–0–(1, 2–DI–0 Palmitoyl–SN–Glycero–3–Phospho)–D–MYO–Inositol 4,5–Biphosphate: An Analogue of Naturally . . . , Tetrahedron Letters, 1988, 29, 6513–6516.
Affinity Labels for Inositol Polyphosphate Receptors, Department of Health and Human Services Grant Application, Jun. 1994.
Reddy et al., Intracellular Mediators: Synthesis of . . . , J. Org. Chem., 1995, 60, 3385–3390.
Prestwich et al., Touching All the Bases: Synthesis of Insositol Polyphosphate and Phosphoinositide Affinty Probes from Glucose, Acc. Chem Res., 1996, 29, 503–513.

*Primary Examiner*—Dwayne C Jones

(57) ABSTRACT

This invention provides analogues of phosphatidylinositol-phosphates modified at one or more selected inositol-hydroxyls and optionally carrying reporter or anchoring groups attached in the lipid or the inositol residues, and, the synthetic intermediates and methods for the preparation of these analogues. The analogues are useful as research reagents in biomedical studies related to structure, function and therapeuticals, including reference materials for analyzing the metabolic products in safety and efficacy studies of 2- and/or 3-hydroxyl modified inositols and phosphatidylinositols as drug candidates.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1, 3-5, 17-20, 24, 30, 39, 42 and 43 is confirmed.

Claims 2, 6-16, 21-23, 25-29, 31-38, 40 and 41 were not reexamined.

* * * * *